US008349364B2

(12) United States Patent
Lively et al.

(10) Patent No.: US 8,349,364 B2
(45) Date of Patent: Jan. 8, 2013

(54) NUCLEIC ACID COATED PARTICLES SUITABLE FOR TEMPORARY STORAGE

(75) Inventors: Chris Robert Lively, Madison, WI (US); Robert DeLong, Chapel Hill, NC (US)

(73) Assignee: Powderject Research Limited, Oxford (GB)

( * ) Notice: Subject to any disclaimer, the term of this patent is extended or adjusted under 35 U.S.C. 154(b) by 736 days.

(21) Appl. No.: 10/529,010

(22) PCT Filed: Sep. 29, 2003

(86) PCT No.: PCT/GB03/04202
§ 371 (c)(1),
(2), (4) Date: Nov. 22, 2005

(87) PCT Pub. No.: WO2004/028560
PCT Pub. Date: Apr. 8, 2004

(65) Prior Publication Data
US 2006/0153804 A1 Jul. 13, 2006

Related U.S. Application Data

(60) Provisional application No. 60/414,097, filed on Sep. 27, 2002.

(51) Int. Cl.
*A61K 9/14* (2006.01)
*A61K 9/16* (2006.01)
*A61K 9/50* (2006.01)
*C12N 15/87* (2006.01)
*C12N 15/11* (2006.01)
*A61K 48/00* (2006.01)

(52) U.S. Cl. ........ 424/489; 435/459; 977/704; 977/722; 514/44 R; 514/44 A

(58) Field of Classification Search .................. None
See application file for complete search history.

(56) References Cited

U.S. PATENT DOCUMENTS

| 4,945,050 | A |   | 7/1990  | Sanford et al. |
|-----------|---|---|---------|----------------|
| 5,120,657 | A |   | 6/1992  | McCabe et al. |
| 5,149,655 | A |   | 9/1992  | McCabe et al. |
| 5,183,658 | A |   | 2/1993  | Lee et al. |
| 5,204,253 | A | * | 4/1993  | Sanford et al. ............... 435/459 |
| 5,630,796 | A |   | 5/1997  | Bellhouse et al. |
| 5,780,295 | A | * | 7/1998  | Livesey et al. ............ 435/307.1 |
| 5,865,796 | A |   | 2/1999  | McCabe |
| 5,945,400 | A |   | 8/1999  | Scherman et al. |
| 6,194,136 | B1 | * | 2/2001 | Livesey et al. ................ 435/1.3 |
| 6,200,956 | B1 |   | 3/2001 | Scherman et al. |
| 6,264,990 | B1 |   | 7/2001 | Knepp et al. |
| 6,288,312 | B1 |   | 9/2001 | Christou et al. |
| 6,641,553 | B1 | * | 11/2003 | Chee et al. ...................... 604/68 |
| 2004/0142475 | A1 | * | 7/2004 | Barman et al. ............... 435/459 |

FOREIGN PATENT DOCUMENTS

| WO | WO 94/24263 A1 | 10/1994 |
| WO | WO 96/04947 A1 | 2/1996 |
| WO | WO 96/12513 A1 | 5/1996 |
| WO | WO 96/20022 A1 | 7/1996 |
| WO | WO 96/25508 A1 | 8/1996 |
| WO | WO 97/40839 A1 | 11/1997 |
| WO | WO 00/02591 A1 | 1/2000 |
| WO | WO 00/26385 A | 5/2000 |
| WO | WO 01/83528 A | 11/2001 |

OTHER PUBLICATIONS

Balhorn, et al. (2000) Molecular Reproduction and Development, 56: 230-34.*
Oard (1993) Plant Cell, Tissue and Organ Culture, 33(3): 247-50.*
Cherng, et al. (1999) Pharmaceutical Research, 16(9): 1417-23.*
Ramos, et al. (1997) Applied and Environmental Microbiology, 63(10): 4020-25.*
Ericksson, et al. (2003) Pharmaceutical Research, 20(9): 1437-43.*
Kaushik, et al. (2003) Journal of Biological Chemistry, 278(29): 26485-65.*
Garg, et al. (2002) Proceedings of the National Academy of Science, USA., 99(25): 15898-903.*
More, et al. (1998) Hindustan Antibiotics Bulletin, 40(1-4): 1-4.*
Joshi, et al. (2001) AAPS PharmSciTech., 2(4): 25.*
Ruan, et al. (2003) European Journal of Biochemistry, 270: 1654-61.*
Schellman (2003) Biophysical Journal, 85(1): 108-25.*
Kwok, et al. (2000) International Journal of Pharmaceutics, 203: 81-88.*
Adami et al., "Stability of Peptide-Condensed Plasmid DNA Formulations," Research Articles, vol. 87, No. 6, Jun. 1998, pp. 676-683.
Almirón et al., "A novel DNA-binding protein with regulatory and protective roles in starved *Escherichia coli*," Genes & Development, vol. 6, 1992, pp. 2646-2654.
Amao et al., "The hydrophobic and electrostatic effect of basic polyamino acid-DNA polyion complex on artificial bilayer lipid membrane," Nucleic Acids Symposium Series No. 29, 1993, pp. 149-151.
Andreasson et al., "Interactions of Spermidine and Methylspermidine with DNA Studied by Nuclear Magnetic Resonance Self-Diffusion Measurements," Biophysical Journal, vol. 70, Jun. 1996, pp. 2847-2856.
Azam et al., "Twelve Species of the Nucleoid-associated Protein from *Escherichia coli*," The Journal of Biological Chemistry, vol. 274, vol. 46, Nov. 12, 1999, pp. 33105-33113.
Baeza et al., "Possible prebiotic significance of polyamines in the condensation, protection, encapsulation, and biological properties of DNA," Origins of Life and Evolution of the Biosphere, vol. 21, 1992, pp. 225-242.

(Continued)

*Primary Examiner* — Robert M Kelly
(74) *Attorney, Agent, or Firm* — Foley & Lardner LLP

(57) ABSTRACT

Particles are provided which are suitable for delivery from a particle-mediated delivery device. The particles are obtained by precipitating a nucleic acid on inert metal carrier particles in the presence of a nucleic acid condensing agent and a metal ion chelating agent. Also described are processes for preparing the particles, and therapeutic methods using the particles including methods of nucleic acid immunization and gene therapy.

47 Claims, No Drawings

OTHER PUBLICATIONS

Bloomfield, Victor A., "Condensation of DNA by Multivalent Cations: Considerations on Mechanism," Biopolymers, vol. 31, 1991, pp. 1471-1481.

Cho et al., "Activation of human neutrophils by a synthetic antimicrobial peptide, KLKLLLLLKLK-NH$_2$, via cell surface calreticulin," Eur. J. Biochem., vol. 266, 1999, pp. 878-885.

DeLong et al., "Novel cationic amphiphiles as delivery agents for antisense oligonucleotides," Nucleic Acids Research, vol. 27, No. 16, 1999, pp. 3334-3341.

Deng et al., "Structural Effects of cobalt-Amine Compounds on DNA Condensation," Biophysical Journal, vol. 77, Sep. 1999, pp. 1556-1561.

Emi et al., "Gene Transfer Mediated by Polyarginine Requires a Formation of Big Carrier-Complex of DNA Aggregate," Biochemical and Biophysical Research Communications, vol. 231, 1997, pp. 421-424.

Fang et al., "Ethanol-induced structural transitions of DNA on mica," Nucleic Acids Research, vol. 27, No. 8, pp. 1943-1949.

Fang et al., "Early Intermediates in Spermidine-Induced DNA Condensation on the Surface of Mica," Journal of the American Chemical Society, vol. 120, No. 35, Sep. 9, 1998, pp. 8903-8909.

Gosule et al., "DNA Condensation with Polyamines, I. Spectroscopic Studies," J. Mol. Biol., vol. 121, 1978, pp. 311-320.

Junghans et al., "Phosphodiester and phosphorothioate oligonucleotide condensation and preparation of antisense nanoparticles," Biochimica et Biophysica Acta, vol. 1544, 2001, pp. 177-188.

Liquier et al., "Infrared Linear Dichroism Investigations of Deoxyribonucleic Acid Complexes with Poly(L-arginine) and Poly(L-lysine)," Biochemistry, vol. 14, No. 19, 1975, pp. 4191-4197.

Martinez et al., "Protection of DNA during Oxidative Stress by the Nonspecific DNA-Binding Protein Dps," Journal of Bacteriology, Aug. 1997, pp. 5188-5194.

McKenzie et al., "Comparative gene transfer efficiency of low molecular weight polylysine DNA-condensing peptides," J. Peptide Res., vol. 54, 1999, pp. 311-318.

Murphy et al., "A combinatorial approach to the discovery of efficient cationic peptoid reagents for gene delivery," Proc. Natl. Acad. Sci. USA, vol. 95, Feb. 1998, pp. 1517-1522.

Park et al., "Topological Defects and the Optimum Size of DNA Condensates," Biophysical Journal, vol. 75, Aug. 1998, pp. 714-720.

Phillips, Stephen C., "Receptor-mediated DNA Delivery Approaches to Human Gene Therapy," Biologicals, vol. 23, 1995, pp. 13-16.

Pouton et al., "Polycation-DNA complexes for gene delivery: a comparison of the biopharmaceutical properties of cationic polypeptides and cationic lipids," Journal of Controlled Release, vol. 53, 1998, pp. 289-299.

Ramsay et al., "Examination of the biophysical interaction between plasmid DNA and the polycations, polylysine and polyornithine, as a basis for their differential gene transfection in-vitro," International Journal of Pharmaceutics, vol. 210, 2000, pp. 97-107.

Schmidt et al., "Cell-free tumor antigen peptide-based cancer vaccines," Proc. Natl. Acad. Sci. USA, vol. 94, Apr. 1997, pp. 3262-3267.

Wolf et al., "DNA protection by stress-induces biocrystallization," Letters to Nature, vol. 400, Jul. 1, 1999, pp. 83-85.

Yang et al., "In vivo and in vitro gene transfer to mammalian somatic cells by particle bombardment," Proc. Natl. Acad. Sci. USA, vol. 87, Dec. 1990, pp. 9568-9572.

Zama et al., "Different effects of polylysine and polyarginine on the transition to a condensed state of DNA in polyethylenegylocol/salt solution," Biochimica et Biophysica Acta, vol. 414, 1976, pp. 256-262.

Fynan et al., "DNA Vaccines: Protective Immunizations by Parenteral, Mucosal and Gene-Gun Inoculations," *Proceedings of the National Academy of Sciences of USA*, Dec. 15, 1993, pp. 11478-11482, vol. 90, No. 24, National Academy of Science, Washington, USA.

\* cited by examiner

NUCLEIC ACID COATED PARTICLES SUITABLE FOR TEMPORARY STORAGE

TECHNICAL FIELD

The present invention relates to nucleic acid coated particles that are suitable for particle-mediated delivery of nucleic acids by a needleless device. In particular, the invention relates to the use of the particles for in vivo and ex vivo delivery of nucleic acid molecules to mammalian tissue.

BACKGROUND

Gene therapy and nucleic acid immunisation are promising approaches for the treatment and prevention of both acquired and inherited diseases. These techniques provide for the transfer of a desired nucleic acid into a subject with subsequent in vivo expression. Transfer can be accomplished by transfecting the subject's cells or tissues ex vivo and reintroducing the transformed material into the host. Alternatively, the nucleic acid can be administered in vivo directly to the recipient. However, the in vivo delivery method must allow the nucleic acid to enter the cells of the recipient so that the nucleic acid can be expressed.

A number of methods have been developed for gene delivery in these contexts. Of these, transdermal delivery of nucleic acids provides many advantages over oral or parenteral delivery techniques. In particular, transdermal delivery provides a safe, convenient and noninvasive alternative to traditional administration systems, conveniently avoiding the major problems associated with oral delivery (e.g. variable rates of absorption, gastric degradation and metabolism, hepatic first pass effect, gastrointestinal irritation and/or bitter or unpleasant drug tastes) or parenteral delivery (e.g. needle pain, the risk of introducing infection to treated individuals, the risk of contamination or infection of health care workers caused by accidental needle-sticks and the disposal of used needles).

However, transdermal delivery of nucleic acids also presents a number of inherent problems. Passive delivery through intact skin entails the transport of molecules through a number of structurally different tissues. These may include the stratum corneum (the major barrier), the viable epidermis, the papillary dermis or the capillary walls in order to gain entry into the blood or lymph system. Transdermal delivery systems must therefore be able to overcome the various resistances presented by each type of tissue.

Therefore, a number of alternatives to passive transdermal delivery have been developed. These alternatives include the use of skin penetration enhancing agents or "permeation enhancers" to increase skin permeability, as well as non-chemical modes such as the use of ionophoresis, electroporation or ultrasound. However, these alternative techniques often give rise to their own side effects such as skin irritation or sensitization.

Recently, particle-mediated techniques suitable for transdermal delivery of nucleic acids have been developed. Particles bearing the nucleic acid of interest are accelerated to high velocity and fired into target tissue using a particle accelerating device. In vivo, the particles may be fired directly into recipient cells, avoiding the need for cell uptake of the passenger nucleic acid.

Various particle acceleration devices suitable for particle-mediated delivery are known in the art. Existing devices employ an explosive, electric or gaseous discharge to propel the coated carrier particles towards target cells. The Biolistic® device, for example, delivers DNA-coated microscopic gold beads directly into the cells of the epidermis (Yang et al (1990) PNAS USA 87:9568-9572). Particles can also be delivered using a needleless syringe device such as that described in U.S. Pat. No. 5,630,796 to Bellhouse et al ("the PowderJect® needleless syringe device").

Particle-mediated devices are intended to allow safe and easy delivery of nucleic acids. However, the physical characteristics of the particles need to be engineered to meet the demands of needleless administration, in which particles are typically fired at very high velocities. The particles need to have a structural integrity such that they can survive the action of, for example, a gas jet of a syringe or ballistic impact with skin or mucosal tissue. It is also important that the particles have a density that enables the particles to achieve sufficient momentum to penetrate tissue. For nucleic acid delivery however, the particles should be smaller than cell size so that they can penetrate cell membranes without disrupting the cells. Nucleic acids are themselves susceptible to degradation on storage. Therefore, the nucleic acid needs to be maintained in stable conditions when associated with the particle. However, the association of the nucleic acid with the particle should also allow efficient expression of the nucleic acid after delivery to the target cell. Where the nucleic acid encodes an antigen, the means of particle association should also allow immunogenicity of the antigen in a subject.

According to one technique, particles suitable for particle mediated delivery can be formed by coating nucleic acid molecules onto inert metal carrier particles. The carrier particles are selected from materials having a suitable density and size, such as tungsten or gold. A number of methods are known for coating or precipitating DNA or RNA onto gold or tungsten particles. These methods generally combine a predetermined amount of gold or tungsten with plasmid DNA, $CaCl_2$ and spermidine. The resulting solution is vortexed continually during the coating procedure to ensure uniformity of the reaction mixture. After precipitation of the nucleic acid, the coated particles can be transferred to suitable membranes and allowed to dry prior to use, coated onto surfaces of a sample module or cassette, or loaded into a delivery cassette for use in particular particle-mediated delivery instruments.

SUMMARY OF THE INVENTION

A new formulation has been developed to optimise both stability of nucleic acid attached to carrier particles, thereby promoting shelf-life of the particles and the quantity of nucleic acid delivered to target cells intact, and also expression and physiological activity of the nucleic acid upon delivery to the target cells. Specifically, it has been found that nucleic acids can be stably attached to inert metal carrier particles in the presence of a nucleic acid condensing agent and a metal ion chelating agent.

The nucleic acid can thus be precipitated onto the carrier particles at neutral rather than alkaline pH, helping to preserve nucleic acid integrity. Furthermore, the particles can then be washed in aqueous or alcoholic solutions without loss of nucleic acid, facilitating incorporation of stability enhancing agents. Condensation of the nucleic acid, together with chemical action of the chelating agent protect the nucleic acid from both physical damage and chemical damage, for example oxidation by free radicals or digestion by endonucleases. The particles of the invention can be delivered to cells by efficient particle mediated delivery. Despite the stability of the nucleic acid particle association, it has been shown that there is efficient expression of the nucleic acid in the target cells. Furthermore immunopotency of nucleic acids encoding antigens has been demonstrated.

Accordingly, the present invention provides particles suitable for delivery from a particle-mediated delivery device, which particles are obtainable by precipitating a nucleic acid on inert metal carrier particles in the presence of a nucleic acid condensing agent and a metal ion chelating agent.

The particle formulation can be further improved by using one or more sugars, and/or salt in particle preparation, and/or by treating particles with an antioxidant such as ethanol or vitamin A, C or E.

The invention also provides:

a process for the preparation of particles suitable for delivery from a particle-mediated delivery device, comprising the steps of:
  (i) precipitating a nucleic acid on inert metal carrier particles in the presence of a nucleic acid condensing agent and a metal ion chelating agent; and
  (ii) collecting the resultant particles;

a method of nucleic acid immunisation comprising
  (a) providing particles suitable for delivery from a particle-mediated delivery device which particles are obtainable by precipitating a nucleic acid encoding an antigen on inert metal carrier particles in the presence of a nucleic acid condensing agent and a metal ion chelating agent; and
  (b) administering an effective amount of the particles to a subject;

a method of gene therapy comprising:
  (a) providing particles suitable for delivery from a particle-mediated delivery device which particles are obtainable by a precipitating a nucleic acid encoding a therapeutic polypeptide on inert metal carrier particles in the presence of a nucleic acid condensing agent and a metal ion chelating agent; and
  (b) administering an effective amount of the particles to a subject; and particles, suitable for delivery from a particle mediated delivery device, which comprise inert metal carrier particles having on their surface a nucleic acid, a metal ion chelating agent and one or more of:
  (i) a nucleic acid condensing agent;
  (ii) one or more disaccharide and/or trisaccharide sugars; and
  (iii) one or more salts.

The invention also provides a dosage receptacle for a particle mediated delivery device, the receptacle containing particles of the invention, as well as a particle mediated delivery device loaded with particles of the invention.

These and other objects, aspects, embodiments and advantages of the present invention will readily occur to those of ordinary skill in the art in view of the disclosure herein.

DETAILED DESCRIPTION OF THE PREFERRED EMBODIMENTS

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of virology, microbiology, molecular biology, recombinant DNA techniques and immunology all of which are within the ordinary skill of the art. Such techniques are explained fully in the literature. See, e.g., Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); and *Fundamental Virology*, 2nd Edition, vol. I & II (B. N. Fields and D. M. Knipe, eds.).

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

A. DEFINITIONS

In describing the present invention, the following terms will be employed, and are intended to be defined as indicated below.

The terms "nucleic acid molecule" and "polynucleotide" are used interchangeably herein and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term nucleic acid sequence is the alphabetical representation of a polynucleotide molecule. This alphabetical representation can be input into databases in a computer having a central processing unit and used for bioinformatics applications such as functional genomics and homology searching.

A nucleic acid sequence which "encodes" a selected antigen is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, procaryotic or eucaryotic mRNA, genomic sequences from viral or procaryotic DNA or RNA, and even synthetic DNA sequences. A transcription termination sequence may be located 3' to the coding sequence.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles. A "plasmid" is a vector in the form of an extrachromosomal genetic element.

A "promoter" is a nucleotide sequence which initiates and regulates transcription of a polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

"Operably linked" refers to an arrangement of elements wherein the components so described are configured so as to perform their usual function. Thus, a given promoter operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

"Recombinant" is used herein to describe a nucleic acid molecule (polynucleotide) of genomic, cDNA, semisynthetic, or synthetic origin which, by virtue of its origin or manipulation is not associated with all or a portion of the polynucleotide with which it is associated in nature and/or is linked to a polynucleotide other than that to which it is linked in nature. Two nucleic acid sequences which are contained within a single recombinant nucleic acid molecule are "heterologous" relative to each other when they are not normally associated with each other in nature.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

An "antigen" refers to any agent, generally a macromolecule, which can elicit an immunological response in an individual. The term may be used to refer to an individual macromolecule or to a homogeneous or heterogeneous population of antigenic macromolecules. As used herein, "antigen" is generally used to refer to a protein molecule or portion thereof which contains one or more epitopes. For purposes of the present invention, antigens can be obtained or derived from any appropriate source. Furthermore, for purposes of the present invention, an "antigen" includes a protein having modifications, such as deletions, additions and substitutions (generally conservative in nature) to the native sequence, so long as the protein maintains sufficient immunogenicity. These modifications may be deliberate, for example through site-directed mutagenesis, or may be accidental, such as through mutations of hosts which produce the antigens.

An "immune response" against an antigen of interest is the development in an individual of a humoral and/or a cellular immune response to that antigen. For purposes of the present invention, a "humoral immune response" refers to an immune response mediated by antibody molecules, while a "cellular immune response" is one mediated by T-lymphocytes and/or other white blood cells.

The term "nucleic acid immunization" is used herein to refer to the introduction of a nucleic acid molecule encoding one or more selected antigens into a host cell for the in vivo expression of the antigen or antigens. The nucleic acid molecule can be introduced directly into the recipient subject by transdermal particle delivery. The molecule alternatively can be introduced ex vivo into cells which have been removed from a subject. In this latter case, cells containing the nucleic acid molecule of interest are re-introduced into the subject such that an immune response can be mounted against the antigen encoded by the nucleic acid molecule. The nucleic acid molecules used in such immunization are generally referred to herein as "nucleic acid vaccines."

The term "transdermal" delivery intends intradermal (e.g., into the dermis or epidermis), transdermal (e.g., "percutaneous") and transmucosal administration, i.e., delivery by passage of an agent into or through skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1-3, Kydonieus and Berner (eds.), CRC Press, (1987). Thus, the term encompasses delivery from a needleless syringe as described in U.S. Pat. No. 5,630,796, as well as particle-mediated delivery as described in U.S. Pat. No. 5,865,796.

By "needleless syringe" is meant an instrument which delivers a particulate composition transdermally without the aid of a conventional needle to pierce the skin. Needleless syringes for use with the present invention are discussed throughout this document.

The terms "individual" and "subject" are used interchangeably herein to refer to any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly.

B. GENERAL METHODS

The invention is concerned with particle-mediated delivery of nucleic acids. In particular, the invention provides particles which are suitable for delivery from a particle-mediated delivery device, and which are obtainable by a process which comprises or which in some embodiments consists essentially of depositing a nucleic acid on inert metal carrier particles in the presence of a nucleic acid condensing agent and a metal ion chelating agent.

The carrier particles are selected from metals which have a suitable density and suitable particle size for intracellular delivery from a particle-mediated delivery device. Preferably, carrier particle density is from about 15 to 25 g/ml for example, from about 15 to 23 g/ml or from about 16 to 20 g/ml. Carrier particles may have diameters of from about 0.5 to 10 µm, for example from about 1 to 5 µm. It is particularly preferred that the carrier particles have a diameter of from about 0.5 to 3 µm, eg from about 1 to 3 µm or 0.5 to 2 µm.

The metal carrier particles are inert in that they are unreactive within the ex vivo cells or the body of the subject to which the particles are to be administered. Typically, gold, tungsten, platinum or iridium carrier particles are used. Gold or tungsten particles are preferred. The gold particles may be colloidal gold particles. Gold particles provide uniformity in size (available from Alpha Chemicals in particle sizes of about 1 to 3 µm, or available from Degussa, South Plainfield, N.J. in a range of particle sizes including 0.95 µm) and reduced toxicity. Microcrystalline gold (e.g., gold powder A1570, available from Engelhard Corp., East Newark, N.J.) provides a diverse particle size distribution, typically in the range of about 0.1 to 5 µm. However, the irregular surface area of microcrystalline gold provides for highly efficient coating with nucleic acids. Tungsten particles are readily available in average sizes of about 0.5 to 2 µm in diameter.

Typically the nucleic acid molecule comprises therapeutically relevant nucleotide sequence for delivery to a subject. It is preferred that the present particles are suitable for use in nucleic acid immunisation or gene therapy. The nucleic acid may thus comprise a sequence capable of providing immunity, for example an immunogenic sequence that elicits a humoral and/or cellular immune response when delivered to a subject. Alternatively, the nucleic acid may comprise one or more genes encoding a therapeutic polypeptide e.g a protein defective or missing from a target cell genome or a non-native protein having a desired biological or therapeutic effect (e.g., an antiviral function). The nucleic acid may comprise sequence that encodes a molecule having an antisense or ribozyme function. For the treatment of genetic disorders, functional genes corresponding to genes known to be deficient in the particular disorder can be administered to a subject. Preferably the nucleic acid is DNA.

Suitable nucleic acids for delivery include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemia and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in anitsense therapy for cancer and for viral diseases have been described in the art. See, e.g., Han et al (1991) *Proc. Natl. Acad. Sci USA* 88:4313; Uhlmann et al (1990) Chem. Rev. 90:543, Helene et al (1990) Biochim. *Biophys. Acta.* 1049:99; Agarwal et al (1988) Proc. *Natl. Acad. Sci. USA* 85: 7079; and Heikkila et al (1987) *Nature* 328:445. A number of ribozymes suitable for use herein have also been described. See, e.g., Chec et al (1992) *J. Biol. Chem.* 267: 17479 and U.S. Pat. No. 5,225,347 to Goldberg et al.

For example, in methods for the treatment of solid tumors, genes encoding toxic peptides (i.e., chemotherapeutic agents such as ricin, diptheria toxin and cobra venom factor), tumor suppressor genes such as p53, genes coding for mRNA sequences which are antisense to transforming oncogenes, antineoplastic peptides such as tumor necrosis factor (TNF) and other cytokines, or transdominant negative mutants of transforming oncogenes, can be delivered for expression at or near the tumor site.

Similarly, nucleic acids coding for polypeptides known to display antiviral and/or antibacterial activity, or stimulate the host's immune system, can also be administered. The nucleic acid may encode one of the various cytokines (or functional fragments thereof), such as the interleukins, interferons and colony stimulating factors. The nucleic acid may encode an antigen for the treatment or prevention of a number of conditions including but not limited to cancer, allergies, toxicity and infection by a pathogen such as, but not limited to, fungus, viruses including Human Papilloma Viruses (HPV), HIV, HSV2/HSV1, influenza virus (types A, B and C), Polio virus, RSV virus, Rhinoviruses, Rotaviruses, Hepatitis A virus, Norwalk Virus Group, Enteroviruses, Astroviruses, Measles virus, Par Influenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola; bacteria including *M. tuberculosis, Chlamydia, N. gonorrhoeae, Shigella, Salmonella, Vibrio Cholera, Treponemapallidua, Pseudomonas, Bordetella pertussis, Brucella, Franciscella tulorensis, Helicobacter pylori, Leptospria interrogaus, Legionella pnumophila, Yersinia pestis, Streptococcus* (types A and B), *Pneuniococcus, Meningococcus, Hemophilus influenza* (type b), *Toxoplama gondic, Complybacteriosis, Moraxella catarrhalis, Donovanosis,* and *Actinomycosis*; fungal pathogens including *Candidiasis* and *Aspergillosis*; parasitic pathogens including *Taenia*, Flukes, Roundworms, *Amebiasis, Giardiasis, Cryptosporidium, Schitosoma, Pneumocystis carinii, Trichomoniasis* and *Trichinosis*. The nucleic acid my also be used to provide a suitable immune response against numerous veterinary diseases, such as Foot and Mouth diseases, Coronavirus, *Pasteurella multocida, Helicobacter, Strongylus vulgaris, Actinobacillus pleuropneumonia,* Bovine viral diarrhea virus (BVDV), *Klebsiella pneumoniae, E. Coli, Bordetella pertussis, Bordetella parapertussis* and *Bordetella brochiseptica*. Thus in one aspect, the particles of the present invention may find use as a vaccine.

The invention will also find use in antisense therapy, e.g., for the delivery of oligonucleotides able to hybridize to specific complementary sequences thereby inhibiting the transcription and/or translation of these sequences. Thus DNA or RNA coding for proteins necessary for the progress of a particular disease can be targeted, thereby disrupting the disease process. Antisense therapy, and numerous oligonucleotides which are capable of binding specifically and predictably to certain nucleic acid target sequences in order to inhibit or modulate the expression of disease-causing genes are known and readily available to the skilled practitioner. Uhlmann et al (1990) *Chem Rev.* 90: 543, Neckers et al (1992) *Int. Rev. Oncogenesis* 3, 175; Simons et al (1992) *Nature* 359, 67; Bayever et al (1992) Antisense *Res. Dev.* 2: 109; Whitesell et al (1991) Antisense Res. Dev. 1: 343; Cook et al (1991) *Anti-cancer Drug Design* 6: 585; Eguchi et al (1991) *Ann. Rev. Biochem.* 60: 631. Accordingly, antisense oligonucleotides capable of selectively binding to target sequences in host cells are provided herein for use in antisense therapeutics.

Typically the nucleic acid is provided as an expression vector. Such expression vectors can be routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of an inserted sequence. Suitable vectors would be apparent to persons skilled in the art. By way of further example in this regard reference is made to Sambrook et al. 1989.

A suitable expression vector comprises a polynucleotide for use in the present invention operably linked to a control sequence, typically a promoter, which is capable of providing for the expression of the polynucleotide by a host cell. Preferably the vector is suitable for use in a method of gene therapy or nucleic acid immunisation. The vector may be used ex vivo, for example to transform a host cell which is then reintroduced into a subject. Alternatively, the vector may be used in vivo for direct delivery to a subject.

The vector is typically a plasmid provided with an origin of replication, a promoter for the expression of the polynucleotide and optionally a regulator of the promoter. The vectors may contain one or more selectable marker genes, for example an ampicillin resistance gene.

Promoters and other expression regulation signals are selected to be compatible with the host cell for which expression is designed. Inducible, repressible or otherwise controllable promoters may be used. For expression in mammalian hosts or mammalian host cells, both eukaryotic and phage control elements may be used.

Suitable mammalian promoters include the metallothionein promoter which can be induced in response to heavy metals such as cadmium and β-actin promoters. Tissue-specific promoters are especially preferred. Suitable viral promoters include for example the Moloney murine leukaemia virus long terminal repeat (MMLV LTR), the Rous Sarcoma virus (RSV) LTR promoter, the SV40 promoter, the human cytomegalovirus (hCMV) immediate early (IE) promoter, adenovirus, HSV promoters (such as the HSV IE promoters), or HPV promoters, particularly the HPV upstream regulatory region (URR). All these promoters are readily available in the art.

Typically, transcription termination and polyadenylation sequences will also be present, located 3' to each translation stop codon. Preferably, a sequence for optimisation of initiation of translation located 5' to each coding sequence is also present. Examples of transcription termination/polyadenylation signals include those derived from SV40, as described in Sambrook et al., as well as a bovine growth hormone terminator sequence. In addition enhancer elements may be included to increase expression levels. Examples of suitable enhancers include the SV40 early gene enhancer (Dijkema et al (1985) EMBO J. 4:761) the enhancer/promoter derived from the long terminal repeat of the Rous Sarcoma Virus (LTR) (Gorman et al (1982) Proc. Natl. Acad. Sci USA 79: 6777) and elements derived from human or murine CMV (Boshart et al (1985) Cell 41:521) for example, elements included in the CMV intron A sequence.

The nucleic acid condensing agent for use in the invention interacts with a nucleic acid in such a way as to condense the nucleic acid into a more compact structure. The condensed nucleic acid is typically more stable than the uncondensed form, and usually has a more ordered structure, for example, a toroidal or rodlike shape. Condensing agents are typically basic molecules, which interact electrostatically with the nucleic acid to counteract its negative charge. It has been reported, for example, that 88-90% charge neutralisation is required for efficient condensation to occur (Deng H. and V. A. Bloomfield (1999) Biophys J 77:1556-61). Usually, the condensing agent binds to the nucleic acid with a relatively high affinity.

Any suitable nucleic acid condensing agent can be used including cationic polymers and multivalent cations. In one embodiment the condensing agent is a cationic polymer or a physiologically acceptable salt thereof. Such pharmaceutically acceptable salts include for example, mineral acid salts such as hydrochlorides, hydrobromides, phosphates, sulphates and the like and salts of organic acids such as acetates, propionates, malonates, benzoates and the like. Typically the salt is a hydrochloride or a sulphate.

Preferably the cationic polymer is a polyamine. Polyamines which may be used include protamines, putrescine, spermidine, spermine, hexadimethrine bromide (Polybrene®) polyarginines and polylysines, or physiologically acceptable salts of the foregoing. The cationic polymer may be a peptide containing a polyamine.

Preferably the polyamine is a cationic polymer of basic amino acids. Typically the basic amino acids are selected from lysine, arginine and histidine. Such polyamino acids are readily available from Sigma-Aldrich.

The polyamino acid may be a homopolymer of a basic amino acid. For example, polyarginine, polylysine or polyhistidine. Alternatively the polyamino acid may be a polymer of one or more basic amino acids, optionally also including one or more non-basic amino acids. Thus the polyamino acid may comprise one or more basic amino acids and optionally one or more other amino acids. Such a copolymer typically comprises a majority of basic amino acids. For example, 50 to 100% of the amino acids in the copolymer may be basic. Preferably 60 to 90% or 70 to 80% are basic. In one embodiment at least 75%, for instance at least 85%, 95%, 98%, or 99% of the amino acids in the copolymer are basic. In general, the basic amino acids comprise one or more of lysine, histidine and arginine. Where the copolymer includes one or more non-basic amino acids, these are preferably not acidic amino acids, such as aspartate or glutamate. The one or more non-basic amino acids may include amino acids with aliphatic or aromatic side chains, for example, threonine, proline, tryptophan, serine or phenylalanine.

The amino acids in any of the above polyamino acids may be L or D amino acids. Preferably, L-amino acids are used.

In a preferred embodiment, the polyamine is a homopolymer of arginine $(Arg)_x$ or lysine $(Lys)_x$. Poly-L-arginine or poly-L-lysine are preferred, in particular poly-L-arginine. Typically, the homopolymer has a molecular weight of from about 500 to 15000, for example from 500 to 10000, from 500 to 5000, or from 500 to 1000. In one embodiment, x in the above formula may range from 2 to 100, for example from 2 to 50, from 2 to 30 or 2 to 20.

Small pepide homopolymers are particularly preferred, for example, those having a molecular weight in the range 500 to 1500, such as 500 to 1250, or 700 to 1000. Typically, in a small peptide, x has a value of from 2 to 10, for example from 4 to 8. Homopolymers where x=4 or 6, for example $(Arg)_4$ or $(Arg)_6$ are especially useful in the present invention.

The condensing agent may be a member of the protamine family of proteins for example, protamine sulphate. Protamines are basic proteins, which occur bound to sperm DNA in place of histones. Sperm nuclei therefore provide an excellent source of protamines e.g. salmine from salmon sperm, clupeine from herring sperm, iridine from trout sperm, sturine from sturgeon sperm and scombrine from mackerel sperm. Protamine, protamine sulphate, protamine phosphate and sperm nucleii are readily available from Sigma-Aldrich.

Other suitable polyamines such as putrescine, spermidine and spermine, together with physiologically acceptable salts thereof are also readily available, for example, from Sigma-Aldrich.

The condensing agent may also comprise multivalent cations or their physiologically acceptable salts. Such multivalent cations include, for example, hexamine cobalt (III) chloride (Cohex), tris(ethylenediamine) cobalt (III) chloride (Coen) and cobalt (III) sepulchrate chloride (Cosep). Suitable physiological salts include those listed above in relation to cationic polymers.

A number of tests are known in the art which can be used to identify nucleic acid condensing agents. These generally assay for a change in the properties of a test nucleic acid molecule where the alteration is associated with the condensation process e.g compaction of the nucleic acid to a solid, neutralisation of the charge of the nucleic acid molecule, or obscuring or blocking of previously accessible recognition sites for agents such as endonucleases and transcription factors.

Assays, indicative of condensation for liquid nucleic acid formulations include but are not limited to: electron and atomic force microscopy, particle size, zeta potential, spectrofluorometric, ethidium bromide exclusion assay, gel shift, circular dichroism and nuclear magnetic resonance. Examples of useful literature citations are: J. Mol Biol (1978) 121, 311-326; Biophysical Journal (1996), 70, 2847-2856, Nucleic Acids Res (1999) 27(8), 1943-1949; J. Amer. Chem. Soc., (1998) 120 (35), 8903-8909; J. Pharm Sci (1998) 87(6), 678-683 and Int. J. Pharm (2000) 210 (1-2), 97-107.

The chelating agent for use in the present invention chelates metal ions from solution. Commonly occurring metal ions for chelation include $Fe^{2+}$, $Fe^{3+}$, $Cr^{3+}$, $Ca^{2+}$ and $Na^+$ ions. Preferably, the agent chelates $Ca^{2+}$ or $Na^+$ ions. Alternatively, it is preferred that the agent chelates $Fe^{2+}$ or $Fe^{3+}$ ions. The agent may be mono- or multi-dentate. For example, suitable agents include but are not limited to ethylenediamine tetraacetic acid (EDTA) diethylenetriamine penta-acetic acid (DTPA), nitrilotriacetic acid (ETA), inositol hexaphosphate, tripolyphosphate, polyphosphoric acid, sodium succinate, potassium succinate, lithium succinate, sodium malate, potassium malate, lithium malate, desferal and ethylenediamine-di (o-hydroxy-phenylacetic) acid (EDDHA). Typically, EDTA, DTPA or desferal is used, in particular EDTA or a salt thereof, for example edetate disodium.

It is also preferred, that the nucleic acid is deposited on the inert metal carrier particles in the presence of one or more disaccharide, and/or trisaccharide sugars. The one or more sugars help to increase the stability of the nucleic acid/metal particle.

Suitable sugars include but are not limited to sucrose, sucrose monolaurate, trehalose, lactose, raffinose and mannitol. Preferably, the sugar is selected from trehalose, sucrose, lactose and raffinose.

In one embodiment, a blend of one or more disaccharide or trisaccharide sugars is used. For example, a blend of one or more of the sugars listed above may be used. A blend of sucrose/raffinose is particularly preferred. Typically, the sucrose/raffinose is blended at a ratio 3:1 wt:wt Nucleic acid may be deposited on the inert metal carrier particle also in the presence of one or more salts. The one or more salts provide still further stability. The salt is in addition to any salt which may be used according to the invention as a chelating agent. Therefore, the salt referred to is in general a non-chelating salt. For example the salt is typically not a malate or a succinate. The salt is also in addition to a physiologically acceptable salt which may be used according to the invention as a nucleic acid condensing agent.

In a preferred embodiment, the one or more salts is selected from chlorides, acetates, citrates, nitrates, phosphates and sulphates. Suitable salts include, but are not limited to potassium acetate, calcium chloride, lithium chloride, sodium acetate, magnesium nitrate, sodium citrate, sodium phosphate, sodium chloride, sodium sulphate and potassium sulphate. Preferably the salt is potassium acetate.

In a preferred embodiment, the nucleic acid bearing particles are contacted with an antioxidant such as ethanol or vitamin A, vitamin C or vitamin E. Typically, treating the particles with the antioxidant increases stability. A typical treatment may involve washing the particles with the antioxidant.

In one embodiment, one or more of the components used in particle preparation becomes incorporated in or associated with the resultant particle. Accordingly, there are provided particles, suitable for delivery from a particle-mediated delivery device, comprising or sometimes consisting essentially of inert metal carrier particles having on their surface a nucleic acid, a metal ion chelating agent and one or more of:

(i) a nucleic acid condensing agent;

(ii) one or more disaccharide and/or trisaccharide sugars; and (iii) one or more salts.

Each of the particle components is as described above. Preferably the particles comprise at least (i) and/or (ii).

The invention also provides a process for the preparation of the present particles. The process comprises or in some embodiments consists essentially of (i) precipitating a nucleic acid on inert metal carrier particles in the presence of a nucleic acid condensing agent and a metal ion chelating agent; and (ii) collecting the resultant particles;

Typically, step (i) comprises contacting the nucleic acid with the inert metal carrier particles in the presence of the nucleic acid condensing agent and the metal ion chelating agent by admixing. It is preferable to vortex the mix continually during the contacting procedure to ensure uniformity of the reaction mixture. Preferably the nucleic acid and nucleic acid condensing agent are separated from each other (eg in separate solutions) until the time when condensation is to occur for example until the carrier particles and chelating agent are also present. It is particularly preferred to add the condensing agent to a mix already comprising the carrier particles and the nucleic acid, to avoid premature precipitation of the nucleic acid. The metal ion chelating agent may then be present in either or both of the condensing agent preparation and the mix of carrier particles and nucleic acid. The condensing agent may be added stepwise, for example dropwise.

Alternatively, a mix of condensing agent and carrier particles may be admixed with a nucleic acid preparation.

The metal particles, nucleic acid, nucleic acid condensing agent and the chelating agent have been described above.

The mix in the precipitation step may additionally include one or more disaccharide and/or trisaccharide sugars, for example, sucrose, sucrose monolaurate, trehalose, lactose, raffinose or mannitol, or a combination thereof. Preferably the sugar is selected from trehalose, sucrose, lactose and raffinose or a combination thereof. A blend of one or more disaccharide and/or trisaccharide sugars may be used. For example a blend of one or more of the above sugars may be used. A blend of sucrose:raffinose is particularly useful, especially at a ratio of 3:1 wt:wt The precipitation mix may also include one or more salts. The salt is in addition to any salt which may be used according to the invention as a chelating agent. Therefore the salt referred to is in general a non-chelating salt. For example the salt is typically not a malate or a succinate. The salt is also in addition to any physiologically acceptable salt which may be used according to the invention as a nucleic acid condensing agent.

In a preferred embodiment, the one or more salts are selected from chlorides, acetates, citrates, nitrates, phosphates and sulphates. Suitable salts include, but are not limited to potassium acetate, calcium chloride, lithium chloride, sodium acetate, magnesium nitrate, sodium citrate, sodium phosphate, sodium chloride, sodium sulphate and potassium sulphate. Typically the salt is not aluminum phosphate. Preferably the salt is potassium acetate.

The sugar/and or salt may be present in either or both of the initial preparations to be admixed, for the example a condensing agent preparation or a carrier particle/nucleic acid preparation.

In one embodiment, a solution comprising predetermined amounts of nucleic acid condensing agent, sugar and metal ion chelating agent is added dropwise to a solution comprising predetermined amounts of metal carrier particles, nucleic acid, sugar and metal ion chelating agent. Salt may be present in either or both solutions.

The concentrations of the components in step (i) may be varied without substantially affecting the stability of the nucleic acid in the resultant particles. The metal carrier particles may present in any suitable amount, for example in a suspension of from 0.1 to 100 mg/ml such as from 0.1 to 10 mg/ml or 1 to 10 mg/ml. Preferably, the nucleic acid concentration is from 0.01 to 10 mg/ml, such as from 0.1 to 1 mg/ml. Typically the condensing agent is at a concentration of from 0.1 to 10 mg/ml, for example, from 0.1 to 1 mg/ml. Preferably the metal ion chelating agent concentration is from 0.1 mM to 1 M, such as from 1 mM to 0.1 M for example 10 to 50 mM. Sugar, if present may be for example, at a concentration of from 0.1 mg/ml to 1 g/ml, preferably from 1 mg/ml to 0.1 g/ml, for example 10 to 50 mg/ml. Salt, if present, is typically at a concentration of from 0.1 mM to 1M for instance from 1 mM to 0.1 M, such as 10 to 50 mM.

The process of the invention may additionally comprise contacting the nucleic acid particles with an antioxidant. Generally this treatment involves washing the particles with a solution of the antioxidant. For example, ethanol may be used. Preferably the ethanol is sucrose saturated. Other suitable antioxidants include vitamin A, vitamin C and vitamin E. Additionally, or alternatively, the nucleic acid particle may be washed one or more times with an aqueous or alcoholic solution such as water or isopropanol.

The coated, optionally washed particles can be transferred to suitable membranes and allowed to dry before use, coated onto surfaces of a sample module or cassette, or loaded into a delivery cassette for use in particular particle-mediated delivery instruments. Any suitable drying method may be used. Preferably drying is carried out under a nitrogen stream.

The particles of the invention may be packaged in single unit dosages or multidose containers. Such containers may comprise an hermetically sealed container enclosing a suitable amount of the particles. The particles can be packaged as a sterile formulation, and the hermetically sealed container can thus be designed to preserve the sterility of the formulation until use in delivery to a subject. The containers are preferably adapted for direct use in a particle mediated delivery device. Typically such containers take the form of capsules, foil pouches, sachets, cassettes and the like. The particle delivery devices can also be provided in a preloaded condition containing a suitable dosage of the coated particles. The preloaded device may then also be prepackaged in a hermetically sealed container.

The container in which the particles are packaged can further be labelled to identify the composition and provide relevant dosage information. In addition, the container can be labelled with a notice in the form prescribed by a governmental agency, for example, the Food and Drug Administration, wherein the notice indicates approval by the agency under Federal Law of the manufacture, use or sale of the nucleic acid preparation contained therein for human administration.

Particle acceleration devices, suitable for particle-mediated delivery are known in the art. Current gene gun devices employ an explosive, electric or gaseous discharge to propel coated carrier particles towards target cells. The coated carrier particles can be releasably attached to a movable carrier sheet, or removably attached to a surface along which a gas stream passes, lifting the particles from the surface and accelerating them toward the target. An example of a gaseous discharge device is described in U.S. Pat. No. 5,204,253. An explosive-type device is described in U.S. Pat. No. 4,945,050. One example of an electric discharge apparatus suitable for use herein is described in U.S. Pat. No. 5,120,657. Another electric discharge apparatus is described in U.S. Pat. No. 5,149,655. The disclosure of all of these patents is incorporated herein by reference in their entireties.

The present coated particles may also be administered using a needleless syringe device, such as those described in U.S. Pat. No. 5,630,796 to Bellhouse et al ("the PowderJect® needleless syringe device") and in International Publication Nos. WO 94/24263, WO 96/04947, WO 96/12513 and WO 96/20022, all of which are incorporated herein by reference.

Devices such as the one described in U.S. Pat. No. 5,630,796 may be provided as a pen-shaped instrument containing, in linear order moving from top to bottom, a gas cylinder, a particle cassette or package, and a supersonic nozzle with an associated silencer medium. The particles are provided within a suitable container, e.g. a cassette formed by two rupturable polymer membranes that are heat-sealed to a washer-shaped spacer to form a self-contained sealed unit. Membrane materials can be selected to achieve a specific mode of opening and burst pressure that dictate the conditions at which the supersonic flow is initiated.

In operation, the device is actuated to release the compressed gas from the cylinder into an expansion chamber within the device. The released gas contacts the particle cassette and, when sufficient pressure is built up, suddenly breaches the cassette membranes sweeping the particles into the supersonic nozzle for subsequent delivery. The nozzle is designed to achieve a specific gas velocity and flow pattern to deliver a quantity of particles to a target surface of predefined area. The silencer is used to attenuate the noise produced by the supersonic gas flow.

The delivery system described in International Publication No. WO 96/20022 also uses the energy of a compressed gas source to accelerate and deliver powdered compositions. However, it is distinguished from the system of U.S. Pat. No. 5,630,796 in its use of a shock wave instead of gas flow to accelerate the particles. More particularly, an instantaneous pressure rise provided by a shock wave generated behind a flexible dome strikes the back of the dome, causing a sudden eversion of the flexible dome in the direction of a target surface. This sudden eversion catapults a powdered composition (which is located on the outside of the dome) at a sufficient velocity, thus momentum, to penetrate target tissue, e.g., oral mucosal tissue. The powdered composition is released at the point of full dome eversion. The dome also serves to completely contain the high-pressure gas flow which therefore does not come into contact with the tissue. Because the gas is not released during this delivery operation, the system is inherently quiet. This design can be used in other enclosed or other wise sensitive applications for example, to deliver particles to minimally invasive surgical sites.

The present coated particles may be delivered in vivo directly to a subject, or ex vivo to cells taken from a subject, the transformed cells then being reimplanted in the subject. For in vivo delivery, particle injection is typically subcutaneously, epidermally, intradermally, intramucosally (e.g. nasally, rectally and/or vaginally), intraperitoneally, intravenously, orally or intramuscularly. Preferably, delivery is to terminally differentiated cells; however, the particles can also be delivered to non-differentiated, or partially differentiated cells such as stem cells of blood and skin fibroblasts. Most preferably, delivery is to skin epidermal cells.

The coated particles are administered to a subject in a manner compatible with the dosage formulation and in an amount that will be prophylactically and/or therapeutically effective. A "therapeutically effective amount" of the present particulate compositions will be sufficient to bring about treatment or prevention of disease or condition symptoms, and will fall in a relatively broad range that can be determined by routine trials. Generally the particles are delivered in an amount of from 0.001 to 1000 µg, more preferably 0.01 to 10.0 µg of nucleic acid per dose. However, the exact amount necessary will vary depending on the age and general condition of the individual being treated and the particular nucleotide sequence selected, as well as other factors. An appropriate effective amount can be readily determined through clinical testing. The "Physicians Desk Reference" and "Goodman and Gilman's The Pharmacological Basis of Therapeutics" are useful for the purpose of determining the amount needed.

C. EXPERIMENTAL

Below are examples of specific embodiments for carrying out the methods of the present invention. The examples are offered for illustrative purposes only, and are not intended to limit the scope of the present invention in any way. Efforts have been made to ensure accuracy with respect to numbers used (e.g. amounts, temperatures, etc.) but some experimental error and deviation should, of course, be allowed for.

Example 1

A series of experiments were carried out to assess the effects of various sugars, chelating agents and other excipients/additives in three DNA/gold particle formulations: "DSEP" (Experiment A) "poly Arg" (experiment B) and "modified spermidine" (experiment C)

The various particles were assessed according to one or more of the following criteria:

(i) DNA yield on particles was measured by elution and by spectrophotometry at A260, or fluorometry (ii) physical stability of DNA on particles was assessed by gel analysis or by HPLC;

(iii) agglomeration of particles was assessed by light microscopy or by actuation into a gel;

(iv) expression activity of DNA on particles was assessed by measuring expression of a luciferase reporter gene in CHO cells following introduction of particles bearing this gene into the cells;

(v) immunopotency of particles was assessed by measuring antibody titres in sera of mice, the mice having been vaccinated with particles bearing DNA encoding an antigen to which the antibody specifically binds.

For each formulation, particles were rank ordered for the above criteria

Experiment A: The DSEP Formulation

Particles were prepared according to the following formula:

Gold particle—DNA—Sugar—Salt—Other

The sugars tested were selected from sucrose monolaurate, mannitol trehalose, lactose, raffinose and sucrose monocaprate. The salts tested were selected from potassium acetate, calcium chloride, lithium chloride, sodium acetate, magnesium nitrate, sodium citrate, sodium phosphate, aluminum phosphate, sodium chloride, sodium sulphate and magnesium chloride.

Various combinations of the sugars and salts were used as set out below. The effect of a wash with sucrose saturated ethanol was also assessed.

Results are shown below, with the various sugars or salts rank ordered for each criterion from the most effective or desirable to the least effective. For example, the top ranking sugars for DNA yield result in relatively high DNA yields; the top ranking sugars for agglomeration result in relatively low levels of agglomeration.

(i) DNA Yield on Particles

Sugar: Sucrose-Sucrose monolaurate~Trehalose~Lactose~Raffinose>>>Sucrose monocaprate (no yield)

Salt: Potassium acetate~Calcium chloride~Lithium chloride~Sodium acetate~Magnesium nitrate>Sodium citrate~Sodium phosphate>>>Aluminium phosphate Other: A wash with sucrose saturated ethanol does not remove DNA from the gold powder The absence of any salt greatly lowers yield (ii) Physical Stability of DNA on Particles Sugar: Sucrose>Trehalose>Mannitol~Lactose~Raffinose>sucrose monolaurate>sucrose monocaprate Salt: Potassium acetate~sodium acetate~sodium citrate~sodium phosphate>sodium chloride>sodium sulfate>lithium chloride Other: A wash with sucrose saturated ethanol contributes to stability Aluminium phosphate prevents precipitation (iii) Agglomeration Sugar: Sucrose monocaprate<Raffinose~Lactose~Sucrose monolaurate<Sucrose~Trehalose Salt: Potassium acetate-Lithium chloride-sodium phosphate~sodium citrate~sodium chloride~sodium sulfate<calcium chloride~magnesium chloride<magnesium nitrate (iv) Expression Activity of DNA on Particles Sucrose/Sodium acetate~Potassium acetate/Raffinose~Sucrose/Magnesium nitrate~Potassium acetate/Sucrose monolaurate (v) Mouse Immunopotency For real-time aged formulas stored at room temperature:

Sucrose/Sodium acetate-Spermidine/$CaCl_2$ nucleic acid particles at 3 months

Raffinose/potassium acetate~Sucrose monolaurate/potassium acetate~Spermidine/$CaCl_2$ nucleic acid particles at 1 month Experiment B: The Poly Arg Formulation Particles were prepared according to the following formula:

Gold particle—DNA—Sugar—Chelating agent—Polyarginine peptide.

The sugars tested were selected from trehalose, sucrose and raffinose. The chelating agents tested were selected from EDTA, DTPA and desferal (DFO). The polyarginine peptides tested were selected from 13000 Mw polyarginine, $(Arg)_6$ and $(Arg)_4$. Various combinations of sugar, chelating agent and polyarginine were tested.

Results are shown below, again in rank order from the most desirable component to the least desirable or effective.
(i) DNA Yield on Particles
Sugars tested: Trehalose, Sucrose, Raffinose
Chelators: EDTA, DTPA, desferal (DFO)
Other: poly-Arg peptides, either 13,000 Mw, $(Arg)_6$, $(Arg)_4$
Yields for all combinations of the above exceed 50% of the theoretical yield.
(ii) Physical Stability of DNA on Particles
Sugar: Sucrose>Trehalose>Raffinose
Chelators: EDTA>DTPA>desferal (DFO)
Other: All poly-Arg peptides gave similar stabilities
(iii) Agglomeration
Not a problem for this formulation
(iv) Expression Activity of DNA on Particles
Trehalose/EDTA/$(Arg)_4$~Trehalose/DTPA/$(Arg)_4$.
Particles prepared using DNA, gold particles and spermidine, showed a similar level of expression activity to these formulations.
(v) Mouse Immunopotency
Sucrose/EDTA/$(Arg)_4$>Trehalose/EDTA/$(Arg)_4$~Trehalose/DTPA/$(Arg)_4$~Sucrose/DTPA/$(Arg)_4$
Particles prepared with DNA, $CaCL_2$ gold particles and spermidine resulted in a similar immunopotency to the Trehalose/EDTA/$(Arg)_4$ particles.

Experiment C: The Modified Spermidine Formulation

Particles were prepared according to the following formula:

Gold particle—DNA—Spermidine—Sugar—Salt—Other.

The sugars tested were selected from sucrose, trehalose and raffinose. Salts tested were selected from magnesium chloride, magnesium nitrate, calcium chloride, sodium sulphate, potassium sulphate and sodium bromide.

The effect of spermidine concentration, and of treating particles with particular water/alcohol solutions was also tested.

Results are shown below.
(i) DNA Yield on Particles
Sugars: Raffinose>Trehalose>Sucrose
Salts: $MgCl_2$~$MgNO_3$~$CaCl_2$>Sodium sulfate~potassium sulfate~sodium bromide
Other: Spermidine concentration and alcohol/water % also affect yield.
(ii) Physical Stability of DNA on Particles
Sugar: Raffinose>Trehalose>Sucrose
Salts: $MgCl_2$>$MgNO_3$>$CaCl_2$>Sodium sulfate~potassium sulfate~sodium bromide
(iii) Agglomeration
Not a problem for this formulation Example 2

Stability Study of Various DNA-Coated Particles

Coated particles were prepared using various ratios of protamine sulphate, EDTA, water and one of trehalose, sucrose or lactose. Particles were prepared according to ten different ratios, as set out in the ten formulae in Table 1. The stability of particles prepared according to each of the ratios was tested at 4° C. and 60° C. and at 0, 7 and 14 day time points.

Method

For each ratio, Tubes A and B were prepared according to Table 1. The contents of Tubes A and B were vortexed at high speed for 10 s, or until each solution was well mixed. While vortexing Tube A at medium speed, the contents of Tube B were added dropwise using a 5 ml pipetman. Tube A was vortexed for a further 15 s, and the contents then allowed to rest for 5 minutes. The supernatant in Tube A was removed and the remaining pellet washed once with 1 ml 100% isopropanol. The contents of the tube were vortexed and pelleted. The isopropanol was removed and the pellet dried to a powder with nitrogen stream.

3-5 mg of each of the particle preparations was weighed into 1.5 ml microcentrifuge tubes for incubation at 4° C. or 60° C. The stability of the DNA in each of the particle preparations was tested at 0, 7, and 14 day time points, by agarose gel electrophoresis and HPLC.

Results

The particle preparations showed similar stability throughout testing. Particles prepared according to "ratio 4" (Formula 4, Table 1) were chosen for further work.

TABLE 1

Experimental DOE used to optimize the sugar and EDTA concentrations for preparation of particles. The numbers across the top of the table are the final concentration of the sugar and EDTA in each tube. The numbers inside the table are in units of μl added to the tubes of each component.

| | | | | | | | | | | | | | |
|---|---|---|---|---|---|---|---|---|---|---|---|---|---|
| Final sugar | (mg/ml) | | 50 | 50 | 50 | 50 | 150 | 150 | 150 | 150 | 100 | 100 | 100 | 100 |
| Final EDTA | (mg/ml) | | 1 | 1 | 5 | 5 | 1 | 1 | 5 | 5 | 3 | 3 | 3 | 3 |

| | | Formula number | | | | | | | | | | | |
|---|---|---|---|---|---|---|---|---|---|---|---|---|---|
| | | 1 | | 2 | | 3 | | 4 | | 5 | | 6 | |
| | | tube a | tube b | tube a | tube b | tube a | tube b | tube a | tube b | tube a | tube b | tube a | tube b |
| gold(24R)(mg) | | 35 | | 35 | | 35 | | 35 | | 35 | | 35 | |
| DNA(mg/ml) | 1 | 70 | | 70 | | 70 | | 70 | | 70 | | 70 | |
| protaminesulphate (mg/ml) | 1 | | 210 | | 210 | | 210 | | 210 | | 210 | | 210 |
| sugar(mg/ml) | 500 | 35 | 35 | 35 | 35 | 105 | 105 | 105 | 105 | 70 | 70 | 70 | 70 |

TABLE 1-continued

Experimental DOE used to optimize the sugar and EDTA concentrations for preparation of particles. The numbers across the top of the table are the final concentration of the sugar and EDTA in each tube. The numbers inside the table are in units of μl added to the tubes of each component.

| edta(mM) | 50 | 7 | 7 | 35 | 35 | 7 | 7 | 35 | 35 | 21 | 21 | 21 | 21 |
|---|---|---|---|---|---|---|---|---|---|---|---|---|---|
| water | | 238 | 238 | 210 | 70 | 168 | 28 | 140 | 0 | 189 | 49 | 189 | 49 |
| Total volume | | 350 | 350 | 350 | 350 | 350 | 350 | 350 | 350 | 350 | 350 | 350 | 350 |
| Final sugar (mg/ml) | | | | | | 25 | 25 | 175 | 175 | 100 | 100 | 100 | 100 |
| Final EDTA (mg/ml) | | | | | | 3 | 3 | 3 | 3 | 0 | 0 | 6 | 6 |

| | | Formula number | | | | | | | |
|---|---|---|---|---|---|---|---|---|---|
| | | 7 | | 8 | | 9 | | 10 | |
| | | tube a | tube b | tube a | tube b | tube a | tube b | tube a | tube b |
| gold(24R)(mg) | | 35 | | 35 | | 35 | | 35 | |
| DNA(mg/ml) | 1 | 70 | | 70 | | 70 | | 70 | |
| protaminesulphate (mg/ml) | 1 | | 210 | | 210 | | 210 | | 210 |
| sugar(mg/ml) | 500 | 17.5 | 17.5 | 122.5 | 122.5 | 70 | 70 | 70 | 70 |
| edta(mM) | 50 | 21 | 21 | 21 | 21 | 0 | 0 | 42 | 42 |
| water | | 241.5 | 101.5 | 136.5 | −3.5 | 210 | 70 | 168 | 28 |
| Total volume | | 350 | 350 | 350 | 350 | 350 | 350 | 350 | 350 |

Example 3

Further Stability Studies Based on Particles Prepared According to "Ratio 4" (Formula 4)

Particles were prepared as in Example 2 and according to ratio 4 in Table 1, but with on a larger scale (350 mg gold particles), and with either
(a) no disaccharide (control); or
(b) trehalose; or
(c) sucrose; or
(d) lactose.

The particles were incubated at 4° C. and 60° C., and the stability of the DNA on the particles assessed after 8 weeks by agarose gel electrophoresis.

Example 4

Development of Tetraarginine Formulations

After trying a few formulae to verify that polyarginines of various lengths have the ability to precipitate DNA onto gold microparticles, an experiment was set up to investigate what polyarginine length to use by studying yields and stabilities. Also investigated were the choice of sugar and chelator, which have been shown to enhance stability in previous formulas.

Results showed that polyarginines of 4 and 6 monomers were better for stability than 13000 molecular weight polymer (about 80 monomers). The sugars and chelators studied performed comparatively. Trehalose and sucrose were both good sugars. EDTA and DTPA were both good chelators. The arginine tetramer was chosen due to its likely quicker dissociation with DNA as well its likelihood to form less degradation products than the 6-mer. The resultant formulae for further study were named TA101.1 (DNA, sucrose, EDTA), TA101.2 (DNA, sucrose, DTPA), TA101.3 (DNA, trehalose, EDTA), TA101.4 (DNA, trehalose, DTPA).

These four formulae were placed on a long-term stability and studied against each other and a Spermidine/CaCl$_2$ control (in which spermidine and calcium chloride were used to precipitate DNA onto gold microparticles) at 4, 25 and 40 degrees Celsius. Their stabilities are shown in Table 2. These formulae were also tested for biological activity in a mouse study and in a luciferase expression experiments (the DNA encoded luciferase).

TABLE 2

| 101 Series Rates of Decay (of SC band) | | | | |
|---|---|---|---|---|
| Formula | Lot # | Temp (° C.) | k (days$^{-1}$) | half life (d) |
| spm/CaCl$_2$ | 2251-45 | 25 | 0.0121 | 57 |
| TA101.1 | 2251-28-I | 25 | 0.0043 | 161 |
| TA101.2 | 2251-28-II | 25 | 0.0092 | 75 |
| TA101.3 | 2251-28-III | 25 | 0.0045 | 154 |
| TA101.4 | 2251-28-IV | 25 | 0.0113 | 61 |
| spm/CaCl$_2$ | 2251-45 | 40 | 0.0373 | 19 |
| TA101.1 | 2251-28-I | 40 | 0.0107 | 65 |
| TA101.2 | 2251-28-II | 40 | 0.0261 | 27 |
| TA101.3 | 2251-28-III | 40 | 0.0117 | 59 |
| TA101.4 | 2251-28-IV | 40 | 0.0421 | 16 |

These activity experiments showed that the 101 series were all active, expressive and about equal to Spermidine/CaCl$_2$. The stabilities of the formulas TA101.1 and TA101.3 were better than TA101.2 and TA101.4. This indicates that the chelator EDTA was more stabilizing than DTPA, but there was little difference between trehalose (3 and 4) and sucrose (1 and 2) as formulated into these powders. The formula compositions of the 101 series of tetraarginine formulas are shown in Table 3.

TABLE 3

101 Series Compositions

| Formula | Sat'd sugar (30% v/v) | Chelator, 5 mM | Ethanol % | (Arg)$_4$ mg/ml |
|---|---|---|---|---|
| TA101.1 | Sucrose | EDTA | 0 | 0.3 |
| TA101.2 | Sucrose | DTPA | 0 | 0.3 |
| TA101.3 | Trehalose | EDTA | 0 | 0.3 |
| TA101.4 | Trehalose | DPTA | 0 | 0.3 |

Next, two experiments were conducted in which saturation levels of trehalose and EDTA were used as the formulation environment. Along with these screens were multiple ethanol levels. These formulations utilized the idea that nearly saturated solutions could precipitate more stabilizers onto the gold. The formulae could be made at different water levels and densities by varying the percent ethanol. The formulae made in these environments seemed more stable than the 101 series of formulae.

An experiment designed to address optimization of ethanol, EDTA, trehalose and tetraarginine levels was then initiated. This experiment was performed under a design that varied four components (tetraarginine, EtOH, EDTA, trehalose) across five levels in specified ranges. A DNA mix was utilized that included 10% luciferase-encoding DNA. This allowed for the study of both stability and activity in one experiment. The optimal formulae were chosen by considering the outcomes, as well as modelling the data to empirical quadratic equations that predict stability and expression outcomes across the whole range of the experiment. The resultant formulae for further study were named TA201.2, TA201.5, TA 201.11 and TA201.15.

The compositions of these four formulae are shown in Table 4. These compositions are the compositions of the formulation environments, i.e. not of final powders. Table 3 shows that these formulae utilize ethanol as a high percent of the solvent. The major difference between 201.5 and 201.11 is trehalose level, but tetraarginine level is also three times higher in 201.5. The only difference between 201.2 and 201.15 is the presence of EDTA in 201.15.

The formula TA201.5 is the optimal formula according to optimization software when expression and stability criteria were optimized simultaneously. TA201.11 is the optimal formula when just stability was optimized. The others are there for comparison. TA201.2 was the most expressive formula and is included in further studies to set a high bar in activity experiments. TA201.15 was the center point of the experiment and was formulated multiple times. This formula therefore had the most repeated stability and activity data, and served as a good anchor to see if the trends repeated themselves when the formulae were studied further.

TABLE 4

201 Series Compositions

| Formula | Trehalose mg/ml | EDTA mM | Ethanol % | (Arg)$_4$ mg/ml |
|---|---|---|---|---|
| TA201.5 | 40.05 | 37.5 | 52.5 | 1.13 |
| TA201.15 | 80.1 | 25 | 35 | 0.75 |
| TA201.11 | 120.15 | 37.5 | 52.5 | 0.38 |
| TA201.2 | 80.1 | 0 | 35 | 0.75 |

Formulae TA201.5, TA201.15 and TA201.11 were very stable. In fact, a 25° C. rate of decay measurement could not be obtained after 6 months of ageing. This temperature is closest to the real condition that the formulae would experience during storage. The stability of TA201.5 was studied at higher temperatures. Comparing relative decay rates at higher temperatures indicates relative stability at lower temperatures. Table 5 shows stabilities of formulae at various temperatures.

TABLE 5

Stabilities of TA's at Various Temperatures

| Lot # | Formula | Temp. | k (days$^{-1}$) | half life (d) |
|---|---|---|---|---|
| 2251-136-sp | spm/CaCl$_2$ | 4 | 0.0052 | 133.3 |
| 2251-136-sp | spm/CaCl$_2$ | 25 | 0.0366 | 18.9 |
| 2251-136-sp | spm/CaCl$_2$ | 40 | 0.2264 | 3.1 |
| 2251-136-2 | TA201.2 | 4 | 0.0071 | 97.6 |
| 2251-136-2 | TA201.2 | 25 | 0.0229 | 30.3 |
| 2251-136-2 | TA201.2 | 40 | 0.2247 | 3.1 |
| 2251-110-15 | TA201.15 | 60 | 0.0437 | 15.9 |
| 2251-110-11 | TA201.11 | 60 | 0.0161 | 43.1 |
| 2334-18-11 | TA201.11 | 60 | 0.0235 | 29.5 |
| 2251-110-5 | TA201.5 | 60 | 0.0362 | 19.1 |
| 2334-80-n | TA201.5 | 60 | 0.0275 | 25.3 |
| 2334-80-m | TA201.5 | 60 | 0.0252 | 27.6 |
| 2251-156-5.1 | TA201.5 | 60 | 0.0528 | 16.4 |
| 2251-156-5.2 | TA201.5 | 60 | 0.0625 | 14.8 |
| 2251-156-5.3 | TA201.5 | 60 | 0.0504 | 13.9 |
| 2334-101-1 | TA201.5 | 60 | 0.0744 | 9.3 |
| 2334-101-2 | TA201.5 | 60 | 0.726 | 9.5 |
| 2334-101-3 | TA201.5 | 60 | 0.0781 | 8.9 |
| 2334-101-4 | TA201.5 | 60 | 0.0645 | 10.8 |
| 2334-101-5 | TA201.5 | 60 | 0.0530 | 13.1 |
| 2334-101-6 | TA201.5 | 60 | 0.0735 | 9.4 |
| 2334-101-7 | TA201.5 | 60 | 0.0514 | 13.5 |
| 2334-101-8 | TA201.5 | 60 | 0.0719 | 9.6 |
| 2334-101-9 | TA201.5 | 60 | 0.0241 | 28.7 |
| 2334-101-10 | TA201.5 | 60 | 0.0163 | 42.6 |
| 2251-136-5 | TA201.5 | 40 | 0.0027 | 253.9 |
| 2251-183-5 | TA201.5 | 40 | 0.0029 | 236.6 |

The physical skin toxicity of formulae TA201.5 and TA201.11 was assessed. No adverse reactions were observed. The activities of the proteins encoded by the DNA in a formula were studied. Luciferase expression was observed when a luciferase-encoding DNA was used. Table 6 shows the results of animal studies in which DNA encoding hepatitis B core antigen (Cag) and hepatitis B surface antigen (Sag) was employed.

TABLE 6

Animal Studies Summary

| Animal study (mouse and time and temperature for which powders aged if appropriate) | SAg ELISA | Cag ELISA | Sag ELISPOT | Cag ELISPOT |
|---|---|---|---|---|
| M103 | 201.5 > Spm | 201.5 ≧ Spm | 201.5 ≦ Spm | n/a |
| M108 | 201.5 ≦ Spm | 201.5 ≧ Spm | 201.5 ≧ Spm | 201.5 ≧ Spm |

TABLE 6-continued

Animal Studies Summary

| Animal study (mouse and time and temperature for which powders aged if appropriate) | SAg ELISA | Cag ELISA | Sag ELISPOT | Cag ELISPOT |
|---|---|---|---|---|
| M110, 0 time | 201.5 ≤ Spm* | 201.5 ≥ Spm* | 201.5 ≥ Spm° | 201.5 ≥ Spm* |
| M110, 1 month @ 25° C. | 201.5 ≥ Spm* | 201.5 = Spm* | 201.5 = Spm* | 201.5 > Spm* |
| M110, 3 months @ 25° C. | 201.5 ≥ Spm* | 201.5 ≥ Spm* | 201.5 ≥ Spm* | 201.5 > Spm* |
| G014 | 201.5 ≥ Spm | 201.5 = Spm | n/a | n/a |
| M114, 3 months @ 25° C. | 201.5 ≤ Spm* | 201.5 ≤ Spm* | 201.5 ≥ Spm* | 201.5 ≥ Spm* |
| M114, 4 months @ 40° C. | 201.5 ≤ Spm* | 201.5 ≥ Spm* | 201.5 ≥ Spm* | 201.5 ≥ Spm* |
| M114, 6 months @ 40° C. | 201.5 ≤ Spm* | 201.5 ≥ Spm* | 201.5 ≥ Spm* | 201.5 ≥ Spm* |
| M116, 2 wks @ 60° C. | 201.5 < Spm | 201.5 ≤ Spm | 201.5 = Spm | 201.5 = Spm |

*These were fresh Spermidine/CaCl$_2$. There were also aged Spermidine/CaCl$_2$ in M110 and M114.

These data clearly indicate that formula TA201.5 was competitive with Spermidine/CaCl$_2$ in terms of antibody ELISA and ELISPOT response assays on ND5.5 transfected animals at a 2 µg DNA dose with a 1 mg of carrier particles load. The formula showed consistent greater or equal to Spermidine/CaCl$_2$ performance with respect to the ELISPOT data (by Mann-Whitney criteria).

The final composition of formula TA201.5 was measured. Table 7 shows the total composition ranges that have been measured from TA201.5 powders.

TABLE 7

TA201.5 Final Total Compositions and Ranges

| Component | µg/mg powder | Chemical Formula, M.W. |
|---|---|---|
| gold micro particles | ~1 mg | Au$_n$, diameter~2 µm |
| pDNA | ~2 | about 5–10K base pairs |
| H-Arg-Arg-Arg-Arg-OH | 0.2–0.8 | C$_{24}$H$_{50}$N$_{16}$O$_5$, 642.8 g/mol |
| *EDTA (4−) | 0.2–1.2 | C$_{10}$H$_{12}$N$_2$O$_8$, 290 g/mol |
| D(+)Trehalose | 1.0–4.0 | C$_{12}$H$_{22}$O$_{11}$*2H$_2$O, 378.3 g/mol |

*EDTA is measured in its 4(−) state, and is reported as a mass of this species (with no sodium, water or hydrogen as seen in the F.W. on the bottle).

Table 8 shows the materials that were used for the manufacture of tetraarginine formulations.

TABLE 8

Materials

| Material | Supplier | Cat. # |
|---|---|---|
| pDNA | GSK, Aldevron, PJV, etc. | N/A |
| Tetaarginine | BaChem | H-4464 |
| Na$_2$EDTA | Sigma | E-7889 |
| Trehalose | Sigma | T-9531 |
| Ethanol | Spectrum | ET107 |
| H$_2$O (for sol'ns) | R.O.D.I. | N/A |
| 10k gold particles | Degussa | RDAU010KM |

The following procedure was used to formulate TA201.5 at a scale of 35 mg gold powder.

Equipment
Scale
Vortexer
Sonicator
Centrifuge
2 ml eppendorf tubes
1 ml, 200 µl pipetmen
Air stream Preparation of Reagents 11.3 mg/ml tetraarginine (lot 523352): Weigh 0.8 to 1.0 mg tetraarginine. Add 88.5 µl H$_2$0 per mg weighed. This will change for lots of different content.

Trehalose Solution: Weigh at least 30 mg trehalose (supplier shown in materials list). Add 120 µl H$_2$0 per 30 mg weighed, or four times the amount of water than trehalose (in mass or µl, since 1 mg/µl).

500 mM Na$_2$EDTA: This can be ordered from Sigma in solution (see materials list for catalog number).

Procedure

Tube B: Have tube B ready before ethanol and DNA are added to tube A. Add the chelator solution, sugar solution, EtOH and tetraarginine solution. Vortex 10 seconds on high.

Tube A: Weigh the gold into the tube. Add the chelator solution and sugar solution. Sonicate 30 seconds, vortex 1 minute on high. Add the EtOH dropwise while vortexing. Add the DNA solution. After DNA is added, add tube B to tube A as described below.

Formulation Steps: While vortexing tube A on medium speed (making sure gold is being mixed throughout the solution) add the contents of tube B dropwise. After all of tube B has been added to tube A, vortex tube A, containing the final tetraarginine formulation, on high for 1 minute. Allow the formulation to settle for 5 minutes. Vortex, then centrifuge for 10 seconds. Pipette out the supernatant, and save it for analysis. Wash the pellet with 250 µl ethyl alcohol. Vortex for 30 seconds, sonicate for 3 seconds. Centrifuge the pellent down for 10 seconds and pull off the ethyl alcohol. Wash the pellet again with 250 µl ethyl alcohol. Vortex for 30 seconds, sonicate for 3 seconds. Centrifuge the pellet down for 10 seconds and pull off the ethyl alcohol. Dry the powder, using an air stream at a flow rate of 0.5 L/min, for 2 hours.

| Tube A | Tube B |
|---|---|
| Gold powder, 35 mg | |
| EDTA, 26.25 µl | EDTA, 26.25 µl |
| Trehalose, 70 µl | Trehalose, 70 µl |
| Sonicate 30 sec, vortex 1 min | tetraarginine, 70 µl |
| EtOH, 183.75 µl dropwise vortexing | EtOH, 183.75 µl |
| DNA, 70 µl | Vortex 10 sec |

Tube A & Tube B
  Add tube B to tube A dropwise while vortexing
  Vortex for 1 minute
  Allow to settle for 5 minutes
  Centrifuge 10 sec and remove supernatant Wash with Ethyl Alcohol, 250 µl, vortex 30 sec, sonicate 3 sec, centrifuge 10 sec, remove Wash with Ethyl Alcohol, 250 µl, vortex 30 sec, sonicate 3 sec, centrifuge 10 sec, remove Dry under air or nitrogen for 2 hours Throughout the development of formula TA201.5, the formulation procedure had been to first make individual stock solutions of each component, then add them to the formulation tubes in a certain order. However, clean-room manufacture of the formula would require a sterile filtration step. A "master mixing" experiment was initiated to address this necessity (NB2334-80). This strategy utilized master mixes of all the aqueous components in tube A (master A) and in tube B (master B). The mixes were then syringe-filtered to sterilize, and the filtered material went into the formulation tubes. The master mixing experiment compared powders made by the master mix procedure and the standard procedure to each other in terms of stability and total composition.

TABLE 9

Final Compositions in Master Mix Experiment

| Powder | DNA yield (%) | Trehalose (µg/mg) | EDTA (µg/mg) | ARG$_4$ (µg/mg) |
|---|---|---|---|---|
| Normal-2334-N | 96.2 | 3.2 | 1.05 | 0.48 |
| Master-2334-M | 96.3 | 3.2 | 0.97 | 0.45 |

TABLE 10

Stabilities of Master vs. Normal
May 21, 2002, t = 18 days

| Formula | ng OC | ng L | Ng SC | Total | % SC | % SC 60/ % SC 4 | t$_{1/2}$ |
|---|---|---|---|---|---|---|---|
| Normal, 4 | 6.1 | 0.7 | 43.5 | 50.3 | 86.5 | | |
| Normal, 60 | 14.5 | 0.5 | 23.1 | 38.1 | 60.7 | 0.70 | 25.3 |
| Master, 4 | 6.3 | 0.8 | 49.2 | 56.2 | 87.5 | | |
| Master, 60 | 24.6 | 1.0 | 31.5 | 57.1 | 55.2 | 0.63 | 27.6 |

Half lives in Table 10 were calculated by averaging two half-life calculations. One was derived from the ng SC rate of decay (60 relative to 4), and the other was derived from the % SC rate of decay (60 relative to 4).

Since the two procedures produced the same final product, the master mixing strategy could be considered non-problematic, and could be used for powder formulation of subsequent TA201.5 powders. A further process experiment was performed in order to decide what process steps were critical:
Experimental: Formulae 1-9 were made at a 70 mg scale from the same stock solutions. A master mix for tube A was made by mixing EDTA, trehalose, and DNA solutions in formulation ratios and then syringe filtered. Master mix for tube B was achieved by mixing EDTA, trehalose, and tetraarginine solutions in formulation ratios, then syringe filtered. Formula 1 was then made by the following process:
Preparation of Reagents (for 10, 70 mg prep)

DNA: Stocks of plasmid and luciferase-encoding DNA were provided at 1 mg/ml. Mix the two DNA solutions at a 9SC18:1 luciferase volume ratio.

1500 µl of SC18+166.7 µl of luciferase DNA.

11.3 mg/ml tetraarginine: Weigh ~20 mg tetraarginine. Add 88.5 µl H$_2$0 per mg weighed.

Trehalose Solution: Weigh at least 700 mg trehalose. Add 140 µl H$_2$0 per 35 mg weighed, or four times the amount of water than trehalose (in mass or µl, since 1 mg/µl).

500 mM EDTA: This can be ordered from Sigma in solution (Cat. E-7889).

Master A Volume Ratios: 1500 µl trehalose, 562.5 µl EDTA, 1500 µl DNA (1 mg/ml)
Syringe filter Master A
Master B Volume Ratios: 1500 µl trehalose, 562.5 µl EDTA, 1500 µl tetraarginine
Syringe filter Master B

| Tube A | Tube B |
|---|---|
| 70 mg gold | |
| 332.5 µl of master mix A | 332.5 µl of master mix B |
| 367.5 µl of EtOH dropwise while vortexing | 367.5 µl of EtOH |
| Sonicate 30 sec, vortex 10 sec | vortex 10 sec |

Tube A & Tube B
Add tube B to tube A dropwise while vortexing
After all of B is added, vortex for 1 minute on high
Allow to settle for 5 minutes
Vortex for 5 sec, then centrifuge for 10 sec, *remove supernatant
Wash with EtOH, 500 µl, vortex 30 sec, sonicate 3 sec, centrifuge 10 sec, *remove
Repeat the last step 1 time
Dry the pellet under air for 1 hour at 0.5 L/min This process is the control formulation. The following Table shows the process variations of powders 2-9.

| Variant step | Formula | Variation | Control |
|---|---|---|---|
| Add'n of B to A | 2 | All of B to A in one squirt | B to A dropwise/ continuous |
| | 3 | B to A dropwise/pause 5 sec between drops | |
| Vortex after B to A | 4 | 3 minute vortex on high | 1 minute vortex on high |
| | 5 | No vortex, allow to settle after all of B added to A | |
| Settling time | 6 | 10 minute settle | 5 minute settle |
| | 7 | No settling, centrifuge after 1 minute vortex | |
| Number of Washes | 8 | 4 washes | 2 washes |
| | 9 | No washes, dry after supernatant removal | |

The remaining formulation was a formula in which the order of addition was changed to assess the possibility of 1 master mix for this formulation. The process was similar to the control.

Master Mix Volume Ratio: 400 µl trehalose, 150 µl EDTA, and 200 µl tetraarginine
Syringe filter Master Mix
Formula 10
70 mg gold
525 µl of master mix
735 µl of EtOH dropwise while vortexing
Sonicate 30 sec, vortex 10 sec
140 µl of DNA dropwise/slowly (pause 5 sec between drops) while vortexing
After all of B is added, vortex for 1 minute on high
Allow to settle for 5 minutes
Vortex for 5 sec, then centrifuge for 10 sec, remove supernatant
Wash with EtOH, 500 µl, vortex 30 sec, sonicate 3 sec, centrifuge 10 sec, *remove Repeat the last step 1 time
Dry the pellet under air for 1 hour at 0.5 L/min
*Removals of liquid from the pellet after centrifugation will be done with a 1000 µl pipette to remove most of the liquid, followed by a 200 µl pipette to remove the rest of the liquid. As little as possible will be left on the powder.

All of the powders were analysed in terms of total compositions, stability, luciferase expression in CHO cells, and gel shots.

TABLE 11

Compositions of Process Robustness Experiment

| Powder | (Arg)$_4$ (μg/mg) | Trehalose (μg/mg) | EDTA (μg/mg) |
|---|---|---|---|
| 2334-101-1 | 0.36 | 1.56 | 0.48 |
| 2334-101-2 | 0.32 | 1.58 | 0.47 |
| 2334-101-3 | 0.36 | 1.72 | 0.46 |
| 2334-101-4 | 0.29 | 1.64 | 0.39 |
| 2334-101-5 | 0.22 | 1.72 | 0.41 |
| 2334-101-6 | 0.26 | 1.54 | 0.41 |
| 2334-101-7 | 0.26 | 2.13 | 0.40 |
| 2334-101-8 | 0.26 | 1.15 | 0.19 |
| 2334-101-9 | 0.23 | 4.77 | 0.99 |
| 2334-101-10 | 0.21 | 2.25 | 0.40 |

TABLE 12

Stabilities at 60° C. of Process Robustness Experiment

| Formula | K | t1/2 (days) |
|---|---|---|
| 1 | 0.0744 | 9.31 |
| 2 | 0.0726 | 9.55 |
| 3 | 0.0781 | 8.88 |
| 4 | 0.0645 | 10.75 |
| 5 | 0.0530 | 13.07 |
| 6 | 0.0735 | 9.43 |
| 7 | 0.0514 | 13.50 |
| 8 | 0.0719 | 9.64 |
| 9 | 0.0241 | 28.75 |
| 10 | 0.0163 | 42.61 |

The above numbers were calculated by changes in nano-grams of super-coiled DNA from the date of formulation to 13 and 20 days.

The rates and half-lives were very close to each other. This indicates that the formulation process is robust in terms of stability. Formulae 5 and 7 had slightly better stabilities than the others, but formulae 9 and 10 had a distinct stability advantage (3×). Formula 9 was not washed (and not feasible to process) and formula 10 was achieved by a change in order of additions.

The expression data indicated that the formulae were very similar (300-400 K counts/sec). The fresh Spermidine/CaCl$_2$ formula were more expressive (or had more expressed material at the time the cells were analyzed) but also measured higher in release mass. Formulae 10 and 7 had some luciferase expression advantage (450-600 K counts/sec) over the other tetraarginine formulae. Overall, the experiment proved the process to be very robust.

Another aspect of robustness is the effect of altering the orders of additions and processes used to make a formula. In one such experiment (NB2251-124) different ways of making a formula with the same exact materials (amounts and concentrations) were investigated. This experiment only looked at stabilities of formulas designed to precipitate components in different orders. This could presumably have large effects since DNA could be precipitated directly to gold before, simultaneously, or after stabilizers.

Formulation Processes:

1. Tubes A and B approach. Tubes A and B have the same composition, except A has DNA, and B has tetraarginine. Both are well mixed, and then B is added to A dropwise.

2. Another tubes A and B approach. This time, in tube A (with gold), the ethanol was added before the DNA sol'n in order to pre-coat the gold with an excess amount of sugar before DNA addition. Then DNA was added to tube A, and tube B was then added to tube A immediately.

3. This approach was designed to simultaneously precipitate DNA and stabilizers. All components were added to one tube except DNA and ethanol. Then, the DNA and ethanol were mixed together and added.

4. This process precipitated DNA prior to ethanol addition. All components were added to one tube except DNA, tetraarginine and ethanol. The order of addition of these last components was DNA, tetraarginine and ethanol respectively.

5. This process was the same as 4 except tetraarginine was added before DNA. Ethanol was still last.

These formulations were placed in 4 and 60 degree incubators, and analyzed 2 weeks after formulation. There were no gross differences between these powders by agarose gel electrophoresis, although powders 4 and 5 (ethanol last, DNA:ARG4 complexation before ethanol) were slightly more stable.

Accordingly, novel nucleic acid coated particles suitable for delivery from a particle-mediated delivery device, a process for preparing the particles, and methods of gene therapy and nucleic acid immunisation using the particles have been described. Although preferred embodiments of the subject invention have been described in some detail, it is understood that obvious variations can be made without departing from the spirit and scope of the invention as defined in the appended claims.

The invention claimed is:

1. Particles suitable for delivery from a particle-mediated delivery device, wherein the particles are obtained by a method comprising the steps of:

(a) depositing a nucleic acid on inert metal carrier particles in the presence of (i) a homopolymer of arginine of the formula of $(Arg)_x$, wherein x is from 2 to 10, or a physiologically acceptable thereof;

(ii) ethylenediamine tetraacetic acid (EDTA); and (iii) drying the particles to a powder.

2. The particles of claim 1, wherein the inert metal carrier particles are selected from the group consisting of gold, tungsten, platinum and iridium particles.

3. The particles of claim 2, wherein the inert metal carrier particles are gold particles having a diameter from about 1 to 3 μm.

4. The particles of claim 1, wherein the nucleic acid encodes an antigen.

5. The particles of claim 4, wherein the antigen is selected from the group consisting of viral antigens, bacterial antigens and fungal antigens.

6. The particles of claim 5, wherein the antigen is a human papilloma virus antigen.

7. The particles of claim 5, wherein the antigen is a HIV antigen.

8. The particles of claim 5, wherein the antigen is a HSV2 or HSV1 antigen.

9. The particles of claim 5, wherein the antigen is a hepatitis B virus antigen.

10. The particles of claim 5, wherein the antigen is an influenza virus antigen.

11. The particles of claim 1, wherein the nucleic acid encodes a therapeutic polypeptide.

12. The particles of claim 1, wherein the nucleic acid is DNA.

13. The particles of claim 1, wherein the homopolymer of arginine is $(Arg)_4$ or $(Arg)_6$.

14. The particles of claim 13, wherein the homopolymer of arginine is $(Arg)_4$.

15. The particles of claim 1, wherein the sugar is one or more disaccharide and/or trisaccharide sugars.

16. The particles of claim 15, wherein the one or more sugars is selected from the group consisting of trehalose, sucrose, lactose and raffinose.

17. The particles of claim 16, wherein the one or more sugars is a blend of sucrose and raffinose.

18. The particles of claim 1, wherein the depositing step is carried out in the presence of one or more salts.

19. The particles of claim 18, wherein the salt is selected from the group consisting of potassium acetate, calcium chloride, lithium chloride, sodium acetate, magnesium nitrate, sodium citrate, sodium phosphate and magnesium chloride.

20. The particles of claim 1, wherein the resultant particles are contacted with an antioxidant.

21. The particles of claim 20, wherein the antioxidant is selected from the group consisting of ethanol, vitamin A, vitamin C and vitamin E.

22. The particles of claim 1, wherein the sugar comprises sucrose.

23. A dosage receptacle for a particle-mediated delivery device, the receptacle containing the particles of claim 1.

24. A particle mediated delivery device loaded with the particles of claim 1.

25. The particle mediated delivery device of claim 24 which is a needleless syringe.

26. The particles of claim of claim 1, wherein the sugar comprises trehalose.

27. A process for preparing the particles of claim 1, comprising:
(i) depositing a nucleic acid on inert metal carrier particles in the presence of
(a) a homopolymer of arginine of the formula of $(Arg)_x$, wherein x is from 2 to 10, or a physiologically acceptable thereof;
(b) ethylenediamine tetraacetic acid (EDTA); and
(c) drying the particles to a powder.

28. The process of claim 27, wherein the homopolymer of arginine is added in step (i) to a mixture comprising the inert metal carrier particles and the nucleic acid.

29. The process of claim 27, wherein the inert metal carrier particles are selected from the group consisting of gold, tungsten, platinum and iridium particles.

30. The process of claim 29, wherein the inert metal carrier particles are gold particles having a diameter from about 1 to 3 μm.

31. The process of claim 27, wherein the nucleic acid encodes an antigen.

32. The process according to claim 31, wherein the antigen is selected from the group consisting of viral antigens, bacterial antigens and fungal antigens.

33. The process according to claim 32, wherein the antigen is an influenza virus antigen.

34. The process of claim 27, wherein the nucleic acid encodes a therapeutic polypeptide.

35. The process of claim 27, wherein the nucleic acid is DNA.

36. The process according to claim 27, wherein the homopolymer of arginine is $(Arg)_4$ or $(Arg)_6$.

37. The process according to claim 36, wherein the homopolymer of arginine is $(Arg)_4$.

38. The process of claim 27, wherein the sugar is one or more disaccharide and/or trisaccharide sugars.

39. The process according to claim 38, wherein the one or more sugars is selected from the group consisting of trehalose, sucrose, lactose and raffinose.

40. The process according to claim 39, wherein the one or more sugars is a blend of sucrose and raffinose.

41. The process according to claim 39, wherein the one or more sugars is trehalose.

42. The process of claim 27, wherein step (i) is further carried out in the presence of one or more salts.

43. The process according to claim 42, wherein the one or more salts is selected from the group consisting of potassium acetate, calcium chloride, lithium chloride, sodium acetate, magnesium nitrate, sodium citrate, sodium phosphate and magnesium chloride.

44. The process of claim 27, wherein the resultant particles from step (i) are contacted with an antioxidant.

45. The process according to claim 44, wherein the antioxidant is selected from the group consisting of ethanol, vitamin A, vitamin C and vitamin E.

46. The process according to claim 27, and the sugar comprises sucrose.

47. The process according to claim 27, wherein the sugar comprises trehalose.

* * * * *

UNITED STATES PATENT AND TRADEMARK OFFICE
CERTIFICATE OF CORRECTION

| | | |
|---|---|---|
| PATENT NO. | : 8,349,364 B2 | Page 1 of 1 |
| APPLICATION NO. | : 10/529010 | |
| DATED | : January 8, 2013 | |
| INVENTOR(S) | : Chris Robert Lively et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 860 days.

Signed and Sealed this
Eighth Day of July, 2014

Michelle K. Lee
*Deputy Director of the United States Patent and Trademark Office*